United States Patent [19]

Carrera et al.

[11] Patent Number: 5,589,501
[45] Date of Patent: Dec. 31, 1996

[54] PHARMACEUTICAL COMPOUNDS

[75] Inventors: Jesus E. Carrera; Almudena R. Esteban, both of Madrid, Spain; André Mann, Ostwald; Angèle Schoenfelder, Lampertheim, both of France; Darryle D. Schoepp, Indianapolis, Ind.; Concepcion P. Tercero, Madrid, Spain; Camille-Georges Wermuth, Strasbourg, France

[73] Assignees: Eli Lilly and Company, Indianapolis, Ind.; Universite Louis Pasteur, Strasbourg Cedex, France; Lilly, S.A., Madrid, Spain

[21] Appl. No.: 343,817

[22] Filed: Nov. 22, 1994

[51] Int. Cl.$^6$ ............ C07C 229/36; C07D 257/04; A61K 31/195; A61K 31/41

[52] U.S. Cl. .......... 514/438; 514/444; 514/648; 548/253; 549/59; 549/76; 549/77; 562/433; 562/441; 562/443; 560/19; 560/36; 560/38

[58] Field of Search ............ 548/253; 549/59, 549/76, 77; 562/433, 441, 443; 514/438, 444, 648; 560/19, 36, 38

[56] References Cited

PUBLICATIONS

08/322/632 Excitatory Amino Acid Receptor Antagonists Filing Date Oct. 13, 1994.
Ohta, Hosoi, and Nozoe, "Stereoselective Hydroxylation of N–Carbamoyl–L–Pyroglutamate. Synthesis of (=)–Bulgecinine", *Tet. Lett.*, 29, 329–332 (1988).
Chang, et al., "Study of the stereoselectivity of L–glutamate receptors by synthetic 4(R)– and 4(S)–substituted L–glutamate analogues", *Brain Research*, 604, 86–89 (1993).
Hon, Chang, and Gong, "Synthesis of (2S,4S) and (2S,4R)–4–Substituted Glutamic Acid Analogues For Neuroexcitatory Activity Studies", *Heterocycles*, 31, 191–195 (1990).
Baldwin, et al., "Stereospecific Amino Acid Synthesis; Preparation of the γ–Anion derived from Glutamic Acid", *J. Chem. Soc., Chem. Commun*, 828–829 (1988).
Cunningham J. Physiol (London) 1985 366. 46–62 [Abstract].
Tetrahedron Letters, vol. 30, No. 29, pp. 3799–3802, 1989, Miwa Yanagida et al., 'Synthesis of acyclic analogues of kainoids and neuroexcitatory activity'.
Tetrahedron Letters, vol. 31, No. 2, pp. 283–284, 1990. Michael R. Attwood et al., 'A new synthetic equivalent of the glutamic acid γanion and its application to the synthesis of S–(+)–γ–carboxyglutamic acid'.
J. Org. Chem., 1991, 56,5729–5733, Isabelle Jako et al, 'Stereoselective synthesis of 3–alkylated glutamic acids: application to the synthesis of secokainic acid'.
*Heterocycles*, vol. 31, No. 2, pp. 191–195, 1990 Hon Yung et al., 'Synthesis of (2S,4S)– and (2S,4SR)–4–substituted glutamic acid analogs for neuroexcitatory activity studies'. Chemical Abstracts, 104, 16856k, 20 Jan. 1986.

*J. Biotechnol*, vol. 3, No. 1–2, pp. 19–31, 1985 H. Zier et al., 'Isolation and characterization of a highly inducible L–aspartate–phenylpyruvate transaminase from *Pseudomonas putida*'.
Chemical Abstracts, 60, 6921A, 16 Mar. 1964.
*Farmaco, Ed. Sci.*, vol. 18, No. 12, pp. 981–989, 1963 M. Artico, 'The synthesis of β–carboxytyrosine'.
Chemical Abstracts, 110, 134597, 10 Apr. 1989.
*Magn. Reson. Chem.*, vol. 26, No. 8, pp. 683–686, 1988 M. Barelle et al., 'Configurational assignment of β–phenylaspartic acids in solution by proton and carbon–13 nuclear magnetic resonance'.
Chemical Abstracts, 116, 211435, 25 May 1992.
*Zh. Evol. Biokhim. Fiziol*, vol. 27, No. 5, pp. 621–625, 1991 Yu E. Mandel'shtam et al., 'The effect of phenyl derivatives of glutamic and aspartic acids on neuromuscular transmission in the locust *Locusta migratoria*'.
Chemical Abstracts, 103, 215754, 23 Dec. 1985.

(List continued on next page.)

*Primary Examiner*—Joseph Conrad
*Attorney, Agent, or Firm*—Martin A. Hay; David E. Boone

[57] ABSTRACT

A pharmaceutical compound of the formula

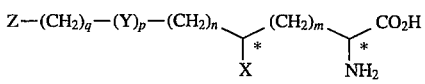

in which m is 0, 1 or 2, n and q are each 0 or 1 to 5, and p is 0 or 1, X is —$CO_2H$ or tetrazolyl, Y is —CH=CH—, and Z is (i) phenyl, naphthyl or thienyl, said phenyl, naphthyl and thienyl being optionally substituted, (ii) —$CHR^1R^2$ where $R^1$ and $R^2$ are each phenyl, naphthyl or thienyl, said phenyl, naphthyl and thienyl being optionally substituted, (iii) =$CR^1R^2$ where $R^1$ and $R^2$ are each phenyl, naphthyl or thienyl, said phenyl, naphthyl and thienyl being optionally substituted, or (iv)

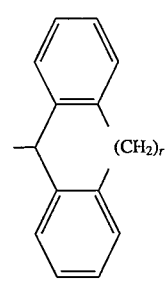

where r is 0 or 1 to 3 and the phenyl rings are optionally substituted;
provided that when Z is phenyl and m is 1, p is 1; and salts and esters thereof.

7 Claims, No Drawings

OTHER PUBLICATIONS

*J. Electrochem. Soc. India,* vol. 34, No. 2, pp. 128–130, 1985 R. K. P. Singh et al., 'Determination of the dissociation constants of α–amino acids by ionophoretic technique; II: amino acids with an additional functional group'.

Chemical Abstracts, 63, 8247g, 27 Sep. 1965.

*Farmaco, Ed. Sci.,* vol. 20, No. 7, pp. 523–531, 1965 M. Artico et al., 'Synthesis of β–carboxy–β–arylalanines'.

Chemical Abstracts, 117, 234488, 7 Dec. 1992.

*Tetrahedron Letters,* vol. 33, No. 33, pp. 4823–4826, 1992 Claudio Palomo et al., 'A concise stereoselective approach to β–lactams via [2+2] cycloaddition reaction of ketenes to glyoxylic ester–derived imines'.

Chemical Abstracts, 114, 164737, 29 Apr. 1991.

*J. Organomet. Chem.,* vol. 401, No. 1–2, pp. C14–C16, 1991 A. Jenhi et al., 'Synthesis of β–and δ–aryl α–amino acids'.

Chemical Abstracts, 113, 24454, 16 Jul. 1990.

*Tetrahedron,* vol. 45, No. 19, pp. 6309–6318, 1989 Jack E. Baldwin et al., 'Non–proteinogenic amino acid synthesis'.

Chemical Abstracts, 113, 24455, 16 Jul. 1990.

*Tetrahedron,* vol. 45, No. 19, pp. 6319–6330, 1989 Jack E. Baldwin et al., 'Non–proteinogenic amino acid synthesis'.

Chemical Abstracts, 96, 218198, 21 Jun. 1982.

*Tetrahedron Lett.,* vol. 22, No. 48, pp. 4863–4866, 1981 John C. Harris et al., 'Abnormal alkylation of N–benzylidene α–amino ester anions with α–halo esters'.

Chemical Abstracts, 85, 47022d, 16 Aug. 1976.

*Rocz. Chem.,* vol. 50, No. 2, pp. 243–249, 1976 M. Bochenska et al., 'Stereochemisty of β–phenylaspartic acids and their derivatives'.

PHARMACEUTICAL COMPOUNDS

This invention relates to novel chemical compounds and their use as pharmaceuticals.

The compounds of the invention have the formula

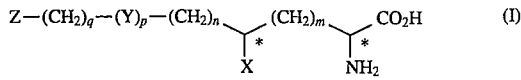
(I)

in which m is 0, 1 or 2, n and q are each 0 or 1 to 5, and p is 0 or 1,

X is —$CO_2H$ or tetrazolyl,

Y is —CH=CH—, and

Z is (i) phenyl, naphthyl or thienyl, said phenyl, naphthyl and thienyl being optionally substituted, (ii) $CHR^1R^2$ where $R^1$ and $R^2$ are each phenyl, naphthyl or thienyl, said phenyl, naphthyl and thienyl being optionally substituted, (iii) —$CR^1R^2$ where $R^1$ and $R^2$ are each phenyl, naphthyl or thienyl, said phenyl, naphthyl and thienyl being optionally substituted, or (iv)

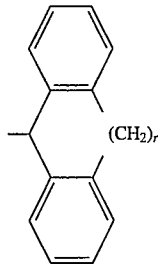

where r is 0 or 1 to 3 and the phenyl rings are optionally substituted;

provided that when Z is phenyl and m is 1, p is 1; and salts and esters thereof.

The compounds of the invention have been found to be active in tests indicative of their use in the treatment of diseases of the central nervous system such as neurological diseases, for example, neurodegenerative diseases, and as antipsychotic, anticonvulsant, analgesic and anti-emetic agents.

In the above Formula (I), an optionally substituted phenyl, naphthyl or thienyl group is optionally substituted with, for example, one or more substituents selected from $C_{1-4}$ alkyl, especially methyl, $C_{1-4}$ alkoxy, especially methoxy and ethoxy, carboxy, hydroxy, cyano, halo, especially bromo, chloro and fluoro, trifluoromethyl, nitro, amino, $C_{1-4}$ acylamino and $C_{1-4}$ alkylthio. An optionally substituted phenyl or naphthyl group can be substituted at neighbouring carbon atoms by —$(CH_2)_4$—. When substituted, a phenyl or naphthyl group is preferably substituted by one to three substituents, and a thienyl group by a single substituent. A naphthyl group can be 1-naphthyl or 2-naphthyl, and a thienyl group can be 2- or 3-thienyl, being preferably 2-thienyl.

When Z is

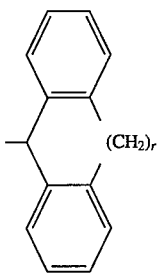

one or both of the phenyl nuclei can be substituted with, for example, one or more substituents as specified above for substituted phenyl. When r is 0 the two benzene nuclei are linked by a single bond. Preferably r is 1 or 2.

Preferred compounds are those which include one or more of the following features:

(i) m is 1, (ii) p is 0, (iii) X is —$CO_2H$, p1 (iv) Z is optionally substituted naphthyl, (v) Z is naphthyl substituted at neighbouring carbon atoms by —$(CH_2)_4$—.

(vi) Z is —$CHR^1R^2$ where $R^1$ and $R^2$ are each optionally substituted phenyl, naphthyl or thienyl, (vii) Z is —$CHR^1R^2$ where $R^1$ and $R^2$ are each optionally substituted phenyl.

It will also be understood that salts of the compounds of the invention can be prepared and such salts are included in the invention. They can be any of the well known base or acid addition salts. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium and sodium salt forms are particularly preferred.

Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example glycollic, maleic, fumaric, malic, tartaric, citric, salicylic or o-acetoxybenzoic acids, or organic sulphonic acids, methane sulphonic, 2-hydroxyethane sulphonic, toluene-p-sulphonic or naphthalene-2-sulphonic acids.

In addition to pharmaceutically-acceptable salts, other salts are included in the invention. They may serve as intermediates in the purification of compounds or in the preparation of other, for example pharmaceutically-acceptable, salts, or are useful for identification, characterisation or purification.

The compounds can also be utilised in ester form, such esters being aliphatic or aromatic, such as, for example, alkyl and phenolic esters. The most preferred esters are alkyl esters derived from $C_{1-4}$ alkanols, especially methyl and ethyl esters.

It will be appreciated that the compounds of the invention contain asymmetric carbon atoms as indicated by the asterisks in formula (I), and this gives rise to diastereoisomers. The compounds can be prepared as racemates or as enantiomers, and individual enantiomers can be isolated from racemates by conventional techniques if so desired. Such racemates and individual enantiomers form part of the present invention.

A preferred group of compounds of Formula (I) above is one which has the enantiomeric structure

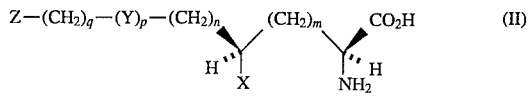

in which each variable has the value given above. Preferably X is —$CO_2H$ and m is 1.

A particularly preferred group of compounds of Formula (I) is as follows

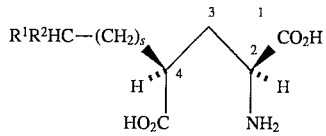

where s is 0 or 1 to 3 and $R^1$ and $R^2$ are both optionally substituted phenyl, and in particular unsubstituted phenyl.

The invention also comprises a process for producing a compound of Formula (I) above, which comprises 1) hydrolysing a compound of the formula

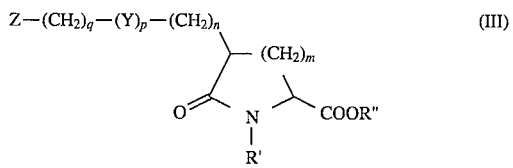

in which m, n, p and q, and Y and Z have the values given above, and R' and R" are protecting groups, to give a compound of Formula (I) in which X is —$CO_2H$, 2) oxidising a compound of the formula

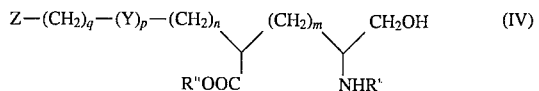

in which m, n, p and q, and Y and Z have the values given above, and R' and R" are protecting groups, to give a compound of Formula (I) in which X is —$CO_2H$, 3) reacting a compound of the formula

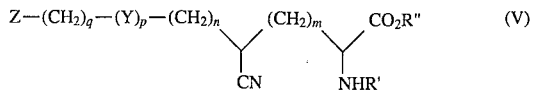

with azide, to give a compound of Formula (I) in which X is tetrazolyl.

The reaction described in process variant (1), above, is one of hydrolysis under conventional hydrolysis conditions using acid or base. It is preferred to use acid. For example, the reaction can be carried out in aqueous medium and in the presence of acid such as for example hydrochloric acid, preferably at a temperature of from 100° C. to 120° C.

Intermediate compounds of Formula (III) can be prepared by reacting a compound of the formula

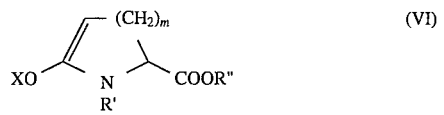

in which X is a metal atom, with an alkylating reagent of the formula Hal $(CH_2)_n$—$(Y)_p$—$(CH_2)_q$—Z (VI) where Hal is a halogen atom, preferably iodine, chlorine or bromine. Compounds of Formula (VI) can, in their turn, be prepared by reacting the appropriate compound of the formula

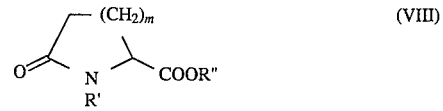

such compounds being readily prepared by known methods, with a metallic reagent preferably lithium hexamethyldisilazide (LiHMDS). It is not essential to separate the metal salt from the reaction medium before carrying out the alkylation reaction. Such reactions are preferably carried out in an inert organic solvent, such as for example tetrahydrofuran, and at a temperature of –100° C. to —50° C.

The alkylation reaction can give rise to a mixture of isomers and the intermediate needed for the preparation of the preferred compounds of the invention can be separated by conventional physical means such as chromatography.

Alternatively, the compound of Formula (VIII) can be reacted with a strong base, such as for example LiHMDS, in the presence of a Lewis acid such as, for example, boron trifluoride etherate, and the appropriate aldehyde, to give an intermediate of the formula

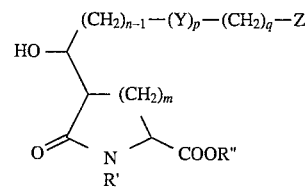

which on activation, for example mesylation, and elimination, gives the olefin, which can be hydrogenated employing a platinum oxide catalyst, to give the intermediate of Formula (III) in cis-form (the two substituents attached to carbon atoms are on the same face of the ring).

The reaction of process variant (2) is preferably carried out in an organic solvent such as for example tetrahydrofuran, at a temperature of –50° C. to –100° C.

The intermediates of Formula (IV) can readily be prepared from known compounds. For example, they can be prepared by ring opening the appropriate oxazolidine of the formula

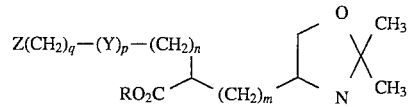

In the above reactions it is frequently necessary to protect the nitrogen atom by means of a protecting group, preferably a carboxy protecting group such as BOG, which can readily be removed when the reaction is completed. Similarly a carboxy group may be protected by conventional groups such as $C_{1-4}$ alkyl.

Compounds of Formula (IX) can be prepared by reaction of a suitable alkylating agent with a compound of the formula

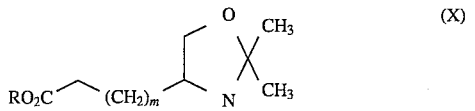

prepared by reducing the corresponding unsaturated compound of formula

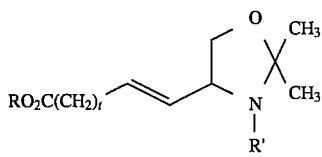

where t is 0 or 1, derived from the aldehyde

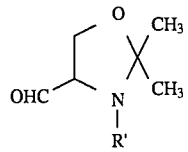

Compounds of Formula (XI) and (XII) are known in the art, and for example are described in J. Org. Chem. 56 (19) 5729–5733 (1991).

With regard to process variant (3), the conversion of nitrile to tetrazolyl (5-tetrazolyl) is preferably carried out employing tributyltin azide, or an alkali metal azide and ammonium chloride, in an organic solent such as dimethylformamide, and preferably at a temperature of from 80° C. to 150° C. The compounds of Formula (V) can be prepared from the prior art compound of Formula (XII) above, disclosed in J. Org. Chem. 56 (19) 5729–5733 (1991) by reaction of appropriate ylid to give a compound of the formula

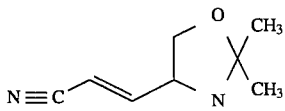

followed by hydrogenation, alkylation and hydrolysing to open the oxazolidine ring.

The compounds described above have pharmaceutical activity. They have been shown to possess affinity for metabotropic glutamate receptors.

Excitatory amino acid or glutamate receptors are subdivided into two types, ionotropic and metabotropic. Ionotropic glutamate receptors are intrinsic ligand gated ion channels that are composed of multiple subunit proteins forming multimeric complexes. Ionotropic glutamate receptors are selectively activated by the agonists N-methyl-D-asparate, AMPA, and kainate (Sommer B. and Seeburg P. H., Trends Pharmacol. Sci. 13: 291–296, 1993). Metabotropic glutamate receptors are a family of G-protein coupled receptors with novel molecular structure that are coupled to increases in phosphoinositide hydrolysis and decreases in cAMP formation. (Schoepp D. D. and Conn J. P., Trends Pharacol. Sci. 14: 13–20, 1993). Metabotropic glutamate receptors can be selectively activated by 1S,3R-1-aminocyclopentane-1,3-dicarboxylic acid (1S, 3R-ACPD).

The affinity of the compounds for metabotropic glutamate receptors has been demonstrated by the selective displacement of 1S, 3R-ACPD-sensitive $^3$H-glutamate binding to rat brain cell membranes, a test for metabotropic glutamate receptor activity described by Schoepp D. D. and True R. A. (Neuroscience Lett. 145: 100–104, 1992). The preferred compounds of the invention have an IC50 value of less than 100 μM. The compounds also block the metabotropic glutamate receptor second messenger responses with IC50 values of less than 100 μM, including stimulation of phosphoinositide hydrolysis by 1S,3R-ACPD (Schoepp D. D., Johnson B. G., True R. A., and Monn J. A., Eur. J. Pharmacol.—Mol. Pharmacol. Section 207:351–353, 1991) and reversal of 1S,3R-ACPD-induced inhibition of forskolin-stimulated cAMP formation (Schoepp D. D., Johnson B. G., and Monn J. A., J. Neurochem. 58:1184–1186, 1992).

The compounds of the invention are thus indicated for use in the treatment of neurological disorders such as acute neurodegenerative diseases, for example stroke, cerebral ischemia and head and spinal cord trauma, and chronic neurodegenerative diseases such as for example Alzheimer's disease, Parkinson's disease, Amyotrophic lateral sclerosis, AIDS-induced dementia and Huntington's Chorea. The compounds are also indicated for use as antipsychotic, anticonvulsant, analgesic and anti-emetic agents. They are also of potential use as anxiolytic and antidepressant agents.

The invention also includes a pharmaceutical composition comprising a pharmaceutically-acceptable diluent or carrier in association with a compound of Formula (I), or a pharmaceutically-acceptable salt thereof.

The compounds may be administered by various routes, for example, by the oral or rectal route, topically or parentally, for example by injection, and are usually employed in the form of a pharmaceutical composition. Such compositions form part of the present invention and are prepared in a manner well known in the pharmaceutical art and normally comprise at least one active compound in association with a pharmaceutically-acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. Where the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydroxbenzoate, talc, magnesium stearate and mineral oil. Compositions in injectable form may, as it is well known in the art, be formulated so as to provide quick, sustained or delayed release of the active ingredient after administration to the patient.

When the compositions are formulated in unit dosage form, it is preferred that each unit dosage form contains from 5 mg to 500 mg, for example, from 15 mg to 200 mg. The term 'unit dosage form' refers to physically discrete units suitable as unit dosages for human subjects and animals. Each unit contains a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range from 5 to 100mg/kg. However, it will be understood that the amount administered will be determined by the physician in the light of the relevant circumstances, including the condition to be treated, the choice of compound to be administered and the chosen route of administration, and therefore the above dosage ranges are not intended to limit the scope of the invention in any way.

The invention is illustrated by the following Examples.

PREPARATION 1

(4R)-1,1-Dimethylethyl-4-(3'-ethoxy-3'-oxo-propanyl)-2,2-dimethyl-3-oxazolidine carboxylate A solution of (4R)-1,1-dimethylethyl-4-(3'-ethoxy-3'-oxo-propenyl)-2,2-dimethyl-3-oxazolidine carboxylate (4.32 g, 0.014 mol) in absolute ethanol (60 ml) was shaken in a Paar bottle, under hydrogen at 70 psi for 16 hours in the presence of Pd/C. The catalyst was filtered over Celite and the solvent evaporated in vacuo. The oil residue was purified by column chromatography on silica gel (ethyl acetate-hexane: 20–80) to yield the above compound.

1,1-Dimethylethyl (4R, 2'R/S)-4-[3'-ethoxy-3'-oxo-2'-(3"-phenyl-2"-propenyl) propyl]-2,2-dimethyl-3-oxazolidinecarboxylate To a solution of freshly distilled diisopropylamine (1.7 ml) in anhydrous tetrahydrofuran (10 ml) under argon was added dropwise a 1.58M solution of n-BuLi (6.33 ml) at −78° C. This mixture was stirred for 30 minutes at 0° C. After cooling at −78° C. HMPT (2 ml) and a solution of carboxylic ester 1,1-dimethyl-(4R)-4-[3'-ethoxy-3'-oxo-propyl]-2,2-dimethyl-3-oxazolidine carboxylate (1.50 g, 5 mmol) in dry tetrahydrofuran (10 ml) were added, and the mixture was allowed to react for 15 minutes at this temperature. A solution of cinnamyl bromide (1.80 g, 9 mmol) in dry tetrahydrofuran (10 ml) was then added dropwise, and stirring continued at the same temperature for 2 hours.

The reaction was quenched with a saturated solution of ammonium chloride and the mixture obtained dried over Na$_2$SO$_4$ and concentrated in vacuo. Purification by column chromatography on silica gel (hexane/Et$_2$O 6/4) afforded the title compound as a colourless oil.

The following compounds were prepared in a similar manner:
1,1-Dimethylethyl (4R, 2'R/S)-4-[3'-ethoxy-3'-oxo-2'-(3"-p-chlorophenyl-2"-propenyl)propyl]-2,2-dimethyl-3-oxazolidinecarboxylate, a colourless oil.
1,1-Dimethylethyl (4R, 2'R/S)-4-(3'-ethoxy-3'-oxo-2'-p-fluorobenzylpropyl)-2,2-dimethyl-3-oxazolidinecarboxylate, a pale yellow oil.
1,1-Dimethylethyl (4R, 2'R/S)-4-(3'-ethoxy-3'-oxo-2'-(1"-naphthylmethyl)propyl]-2,2-dimethyl-3-oxazolidinecarboxylate, a colourless oil.

PREPARATION 2

Ethyl (2R/S, 4R)-2-(3'-phenyl-2'-propenyl)-4[[(1,1)-dimethylethoxy)carbonyl]amino]-5-hydroxypentanoate A solution of 1,1-dimethylethyl (4R, 2'R/S)-4-[3'-ethoxy-3'-oxo-2'-(3"-phenyl-2"-propenyl)propyl]-2,2-dimethyl-3-oxazolidinecarboxylate and pyridinium p-toluene sulfonate in methanol was refluxed for 3–4 hours. The solvent was evaporated in vacuo and the oily residue obtained was purified by column chromatography on silica gel. The product was a colourless oil.

The following compounds were prepared in a similar manner.
Ethyl (2R/S, 4R)-2-(3'-p-chlorophenyl-2'-propenyl)-4[[(1,1)-dimethylethoxy)carbonyl]amino]-5-hydroxypentanoate, a colourless oil.
Ethyl (2R/S, 4R)-2-p-fluorobenzyl-4[[(1,1)-dimethylethoxy)carbonyl]amino]-5-hydroxypentanoate, a colourless oil
Ethyl (2R/S, 4R)-2-(1'-naphthylmethyl)-4[[(1,1)-dimethylethoxy)carbonyl]amino]-5-hydroxypentanoate, a colourless oil

PREPARATION 3

1-Methyl 5-ethyl (2R, 4R/S)-2-[[1,1-dimethylethoxy)carbonyl]amino]4-(3'-phenyl-2'-propenyl)-1,5-pentanedioate A solution of the amino alcohol, ethyl (2R/S, 4R)-2-(3'-phenyl-2'-propenyl)-4[[(1,1)-dimethylethoxy)carbonyl]amino]-5-hydroxypentanoate, in dimethylformamide (70 ml) was stirred under argon with pyridinium dichromate for 16 hours. The reaction mixture was diluted with water (250 ml), acidified to pH 2 with 10% aqueous HCl and extracted with ether (3×150 ml). The combined organic layers were washed with brine, dried over Na$_2$SO$_4$, and concentrated under vacuum. The oily residue was dissolved in ether and treated with diazomethene/ether at 0° C. Evaporation of the solvent and purification of the crude product by column chromatography (ether/hexane 6/4) afforded the diester as a colourless oil.

The following compounds were prepared in a similar manner:
1-Methyl 5-ethyl (2R, 4R/S)-2-[[(1,1-dimethylethoxy)carbonyl]amino]4-(3'-p-chlorophenyl-2'-propenyl)-1,5-pentanedioate, a colourless oil
1-Methyl 5-ethyl (2R, 4R/S)-4-p-fluorobenzyl-2-[[(1,1-dimethylethoxy)carbonyl]amino]-1,5-pentanedioate, a colourless oil
Ethyl (2R, 4R/S)-2-[[(1,1-dimethylethoxy)carbonyl]amino]4-(1'-naphthylmethyl)-1,5-pentanedioate, a colourless oil

EXAMPLE 1

(2R, 4R/S)-2-Amino-4-(3'-phenyl-2'-propenyl)-1,5-pentanedioic acid

To a solution of the diester, 1-methyl 5-ethyl (2R, 4R/S)-2-[[1,1-dimethylethoxy)carbonyl]amino]4-(3'-phenyl-2'-propenyl)-1,5-pentanedioate in 1,2-dimethoxyethane (8 ml) was added a 2.5N aqueous solution of LiOH (7.2 ml). The mixture was stirred at room temperature for 5 hours, then acidified to pH 1 with concentrated HCl and extracted with ethyl ether (3×10 ml). The combined organic layers were dried over Na$_2$SO$_4$ and concentrated in vacuo to yield an oily residue, which was reacted with trifluoroacetic acid (11 ml) at 0° C. for 45 minutes. Water (4 ml) was added and the mixture was concentrated in vacuo to give a pale yellow oil. This oil was dissolved in water (15 ml). The solution was washed with ethyl ether (3×5 ml), concentrated in vacuo and the oily residue obtained treated with ethyl ether. The resulting white solid (119 mg) was purified by ion-exchange chromatography (Dowex 50×8-100 ion-exchange resin) eluting with 7% pyridine solution. The product was a white solid, m.p. 146°–147° C.

The following compounds were prepared in a similar manner.
(2R, 4R/S)-2-Amino-4-(3'-p-chlorophenyl-2'-propenyl)-1,5-pentanedioic acid, a white solid, m.p. 157° C.
(2R, 4R/S)-2-Amino-4-p-fluorobenzyl-1,5-pentanedioic acid, a white solid, m.p. 147°–148° C.
(2R, 4R/S)-2-Amino-4-(1'-naphthylmethyl)-1,5-pentanedioic acid, a white solid, m.p. 180°–182° C.

EXAMPLE 2

Synthesis of the two diastereoisomers of 2-amino-4-(3'-phenyl-2'-propenyl)-1,5-pentanedioic acid.

1-Methyl 5-ethyl (2R, 4R/S)-2-amino-4-(3'-phenyl-2'-propenyl)-1,5-pentanedioate

The N-protected compound, 1-methyl 5-ethyl (2R, 4R/S)-2-[[1,1dimethylethoxy)carbonyl]amino]4-(3'-phenyl-2'-propenyl)-1,5-pentanedioate (770 mg) was reacted with trifluoroacetic acid (12 ml) at 0° C. for 45 minutes. Water (5 ml) was added and the mixture was concentrated in vacuo to yield an oily residue. Water (30 ml) and a saturated solution of $K_2CO_3$ were added until pH 8. The solution obtained was extracted with ether (3×30 ml) and concentrated in vacuo. The resulting oil was purified by column chromatography (eluent: $CH_2Cl_2$/acetone 85/15).

2) Methyl (2R, 4R)-4-(3'-phenyl-2'-propenyl)pyroglutamate and methyl (2R, 4S)-4-(3'-phenyl-2'-propenyl)pyroglutamate A solution of 514 mg of the compound of (1) above (1.69 mmol) in toluene was refluxed for 4 hours. The solvent was removed in vacuo. Purification of the crude product was separated by column chromatography to give the two diastereoisomers as white solids, m.p. 88°–89° C. and 110°–112° C., respectively.

3) Methyl (2R, 4S)-1-(tert-butyloxycarbonyl)-4-(3'-phenyl-2'-propenyl)pyroglutamate To a solution of the 2R, 4S compound of (2) above (150 mg) in $CH_2Cl_2$ (4 ml) were added triethylamine (0.084 ml), di-t-butyl dicarbonate (254 mg) and DNAP (72 mg). The mixture was stirred for 20 hours. The solvent was removed in vacuo. 1N HCl was added (20 ml) and the mixture extracted with ether (3×20 ml). The combined organic layers wore dried over $Na_2SO_4$ and the solvent evaporated in vacuo. Purification of the crude product by column chromatography (diethyl ether/hexane: 7/3) afforded the above as a white solid, m.p. 100°–101° C. Methyl (2R, 4R)-1-(tert-butyloxycarbonyl)-4-(3'-phenyl-2'-propenyl)pyroglutamate, a white solid, m.p. 135°–136° C., was prepared in a similar manner.

4) (2R, 4S)-2-Amino-4-(3'-phenyl-2'-propenyl)-1,5-pentanedioic acid

To a solution of the 2R, 4S compound of (3) above (145 mg) in 1,2-dimethoxyethane (4 ml) was added a 2.5N aqueous solution of LiOH (2.0 ml, 4.8 mmol, 12 equiv.) The mixture was stirred at room temperature for 5 hours, then acidified to pH 1 with HCl and extracted with ether (3×10 ml). The combined organic layers were dried over $Na_2SO_4$ and concentrated in vacuo to give an oily residue, which was reacted with a 1/1 mixture of TFA/$CH_2Cl_2$ (10 ml) at room temperature for 3 hours. Water (4 ml) was added and the mixture concentrated in vacuo. The crude product was purified by ion exchange chromatography, to give a white solid, m.p. 157°–159° C.

(2R, 4R)-2-Amino-4-(3'-phenyl-2'-propenyl)-1,5-pentanedioic acid, a white solid, m.p. 153°–154° C., was prepared in a similar manner.

PREPARATION 4

General procedure for alkylation reactions on ethyl N-tert. butoxycarbonyl pyroglutamate.

To a solution of the pyroglutamate (7.77 mmol) in dry tetrahydrofuran (40 ml) under argon was added a 1M solution of lithium hexamethyldisilazide in dry tetrahydrofuran (8.55 ml) at −78° C. After one hour a solution of the electrophile (9.30 mmol) in dry tetrahydrofuran (10 ml) was added, and stirring was continued for 2 hours. The reaction mixture was quenched with saturated ammonium chloride solution (50 ml) at −78° C. and extracted with ethyl ether (3×20 ml). The combined organic phases were dried over $Na_2SO_4$, filtered and evaporated to dryness. The diastereomeric mixtures were separated by flash column chromatography (the eluent is indicated in each case), as follows:

(2S, 4R)-1-(tert-Butoxycarbonyl)-4-cinnamyl ethylpyroglutamate: (hexane/ethyl acetate: 3:1). Colourless oil.

(2S, 4S)-1-(tert-Butoxycarbonyl)-4-cinnamyl ethylpyroglutamate. Colourless oil.

(2S, 4R)-1-(tert-Butoxycarbonyl)-4-(2-naphthylmethyl) ethylpyroglutamate: (hexane/ethyl acetate 4:1). White needles, m.p. 124°–4° C. (hexane).

PREPARATION 5

General procedure for aldol reactions on ethyl N-tert. butoxycarbonyl pyroglutamate and further treatment of the resulting aldol mixtures with MsCl and $Et_3N$.

To a solution of the pyroglutamate (15.6 mmol) in dry tetrahydrofuran (50 ml) stirred at −78° C. was added a 1M solution of lithium hexamathyldisilazide in dry tetrathydrofuran (18.7 ml). The reaction mixture was stirred for one hour at −78° C. prior to the addition of a solution of the aldehyde (17.2 mmol) and $BF_3OEt_2$ (17.2 mmol) in dry tetrahydrofuran (50 ml). The reaction mixture was stirred for one hour at −78° C. and then quenched with saturated ammonium chloride solution (100 ml) and extracted with ethyl ether (3×50 ml). The combined organic phases were dried over $Na_2SO_4$, filtered and evaporated to dryness. The reaction crude was dissolved in $CH_2Cl_2$ (30 ml) and treated with methanesulfonyl chloride (1.34 ml) and triethylamine (18 ml). After stirring this solution for three days at room temperature it was quenched with water and extracted with dichloromethane (3×50 ml). The organic layer was dried over $Na_2SO_4$ and evaporated under reduced pressure affording compounds as mixtures of E/Z isomers. The eluent is indicated in the cases where chromatographic separation was carried out, as follows:

(2S, E)-1-(tert-Butoxycarbonyl)-4-(2-naphthylmethylidene) ethylpyroglutamate: (hexane/ethyl acetate 3:1). White needles, m.p. 177°–178° C.

(2S, E)-1-(tert-Butoxycarbonyl)-4-anthrylmethylidene ethylpyroglutamate: (hexane/ethyl acetate 3:1). Yellow solid, m.p. 62°–63° C.

(2S, E)-1-(tert-Butoxycarbonyl)-4-(2,2-diphenylethylidene) ethylpyroglutamate: (hexane/ethyl acetate 3:1). Colourless oil.

(2S, E)-1-(tert-Butoxycarbonyl)-4-(3,3-diphenylpropylidene) ethylpyroglutamate: (hexane/ethyl acetate 3:1). Colourless oil.

(2S, Z)-1-(tert-Butoxycarbonyl)-4-(3,3-diphenylpropylidene) ethylpyroglutamate: (hexane/ethyl acetate 3:1). Colourless oil.

(2S, E)-1-(tert-Butoxycarbonyl)-4-(4,4-diphenylbutylidene) ethylpyroglutamate: (hexane/ethyl acetate 4:1). Colourless oil.

(2S, Z)-1-(tert-Butoxycarbonyl)-4-(4,4-diphenylbutylidene) ethylpyroglutamate: (hexane/ethyl acetate 4:1). Colourless oil.

(2S, E)-1-(tert-Butoxycarbonyl)-4-(5,5-diphenylpentylidene) ethylpyroglutamate: (hexane/ethyl acetate 4:1). Colourless oil.

PREPARATION 6

General procedure for the hydrogenation reactions of 4-alkylidene and 4-alkenyl pyroglutamate ethyl esters.

$PtO_2$ (0.65 mmol) was added to a solution of the title compounds (6.46 mmol) in ethyl acetate (50 ml). Hydrogen (1 atm) was introduced and the heterogeneous mixture was stirred at room temperature for four hours. The mixture was filtered through a pad of celite and evaporated to give the hydrogenated compounds. Hydrogenation of 4-alkylidene ethylpyroglutamates following this procedure gave exclusively the cis isomers, as follows:

(2S, 4S)-1-(tert-Butoxycarbonyl)-4-(2-naphthylmethyl) ethylpyroglutamate: White solid, m.p. 112°–113° C. (hexane/ethyl acetate).

(2S, 4S)-1-(tert-Butoxycarbonyl)-4-(1,2,3,4-tetrahydro)anthrylmethyl ethylpyroglutamate: White solid, m.p. 64°–65° C. (hexane/ethyl acetate).

2S, 4S)-1-(tert-Butoxycarbonyl)-4-(2,2-diphenylethyl) ethylpyroglutamate: (hexane/ethyl acetate 4:1). Colourless oil.

(2S, 4S)-1-(tert-Butoxycarbonyl)-4-(3,3-diphenylpropyl) ethylpyroglutamate: (hexane/ethyl acetate 3:1). Colourless oil.

(2S, 4S)-1-(tert-Butoxycarbonyl)-4-(4,4-diphenylbutyl) ethylpyroglutamate: (hexane/ethyl acetate 4:1).

(2S, 4S)-1-(tert-Butoxycarbonyl)-4-(5,5-diphenylpentyl) ethylpyroglutamate: (hexane/ethyl acetate 4:1). Colourless oil.

PREPARATION 7

General procedure for the equilibration of cis 4-substituted ethylpyroglutamates.

A solution of the title compound (1 mmol) and KCN (1 mmol) in DMF (8 ml) was stirred at room temperature for seven days. The reaction mixture was diluted with water (15 ml) and extracted with ethyl ether (3×8 ml). The organic layer was dried over $Na_2SO_4$ and evaporated to dryness. The diastereomeric mixtures (trans/cis ratio~2/1) were separated by flash chromatography. The eluent is indicated in each case.

(2S, 4R)-1-(tert-Butoxycarbonyl)-4-(2-phenylethyl) ethylpyroglutamate: (hexane/ethyl acetate 4:1). White solid, m.p. 81°–82° C.

(2S, 4R)-1-(tert-Butoxycarbonyl)-4-(4-phenylbutyl) ethylpyroglutamate: (hexane/ethyl acetate 5:1).

EXAMPLE 3

General procedures for the hydrolysis of 4-substituted N-BOC ethylpyroglutamates. Synthesis of λ-alkyl glutamic acid hydrochlorides:

METHOD A. A mixture of the title compounds (2 mmol) and a 6N HCl solution (25 ml) was refluxed over night. The resulting solution was evaporated to dryness yielding a white solid which was triturated with ethyl ether (3×20 ml).

METHOD B. To a solution of the title compounds (2 mmol) in tetrahydrofuran (15 ml) was added a 2.5N aqueous solution of LiOH (14.4 ml, 36 mmol). The mixture was stirred at room temperature for four hours, then acidified to pH 2 with 1N HCl solution and extracted with ethyl ether (3×20 ml). The combined organic layers were dried over $Na_2SO_4$ and concentrated in vacuo to give an oily residue which was reacted with a saturated HCl solution in ethyl acetate for one hour at room temperature. The resulting white solid was triturated with ethyl ether (3×20 ml).

(2S, 4R)-2-Amino-4-(2-naphthylmethyl)pentanedioic acid hydrochloride. Method A. White solid, m.p. 144° C.

(2S, 4S)-2-Amino-4-(2-naphthylmethyl)pentanedioic acid, hydrochloride. Method A. White solid, m.p. 199°–200° C.

(2S, 4S)-2-Amino-9-(1,2,3,4-tetrahydro)anthrylmethyl pentanedioic acid. Method B. White solid, m.p. 142°–144° C.

(2S, 4S)-2-Amino-4-(2,2-diphenylethyl)pentanedioic acid, hydrochloride. Method A. White solid, m.p. 160°–162° C.

(2S, 4S)-2-Amino-4-(3,3-diphenylpropyl)pentanedioic acid, hydrochloride. Method A. White solid, m.p. 129°–130° C.

(2S, 4S)-2-Amino-4-(4,4-diphenylbutyl)pentanedioic acid, hydrochloride. Method A. White solid, m.p. 149°–150° C.

(2S, 4S)-2-Amino-4-(5,5-diphenylpentyl)pentanedioic acid, hydrochloride. Method A. White solid, m.p. 150°–151° C.

(2S, E)-2-Amino-4-(4,4-diphenylbutylidene)pentanedioic acid, hydrochloride. Method S. White solid, m.p. 155°–157° C. (dec).

(2S, Z)-2-Amino-4-(4,4-diphenylbutylidene)pentanedioic acid, hydrochloride. Method B. White solid, m.p. 196°–198° C. (dec).

EXAMPLE 4

1) (4S)-1,1-Dimethylethyl-4-[(E)-2'-cyano-1'-ethenyl]-2,2-dimethyl-3-oxazolidine carboxylate A mixture of a serinal N,O-diprotected (R)-serinal compound (2 g, 8.7 mmol), diethylcyanomethyl phosphonate (3 g, 17.5 mmol, 2.75 ml), n-$Bu_4N^+I^-$ (500 ml, 1.5 mmol) and 3M aqueous $K_2CO_3$ (4.4 ml) was stirred at room temperature for 12 hours. The mixture was then diluted with $H_2O$ (50 ml) and extracted with ether (3×15 ml). The combined extracts were washed with brine, dried ($Na_2SO_4$) and concentrated in vacuo to an oil which was purified by column chromatography on silica gel ($Et_2O$/hexane: 25/75) to give the above compound as an oil.

2) (4S)-1,1-Dimethylethyl-4-(2'-cyanoethyl)-2,2-dimethyl-3-oxazolidinecarboxylate A solution of the compound of (1) (1.67 g, 6.62 mmol) in anhydrous ethanol (20 ml) was hydrogenated with 10% Pd/C (30 mg) at 60 psi for 5 hours. The mixture was filtered and concentrated in vacuo. The oil residue was purified by chromatography on silica gel ($Et_2O$/hexane: 6/4) and identified as the title compound.

3) Preparation of 1,1-diphenyl-4-iodobutane

A mixture of 1,1-diphenyl-4-bromobutane (2.5 g, 12 mmol) and NaI (11.9 g, 80 mmol) in 2-butanone (70 ml) was heated for 4 hours at reflux. The solvent was removed in vacuo and the residue was taken up in $Et_2O$ (100 ml). The organic layer was washed with aqueous $Na_2SO_3$ (10%) and with brine, dried ($Na_2SO_4$), and concentrated in vacuo. The oil was distilled under high vacuum to obtain the title compound, bp 150° C./0.1 mm.

4) (4S, 2'R and S)-1,1-Dimethylethyl-4-[2'-cyano-2'-(4", 4"-diphenylbutyl)ethyl]2,2-dimethyl-3-oxazolidine carboxylate To a solution of freshly distilled diisopropylamine (0.14 ml, 1 mmol, 1.3 equiv.) in anhydrous THF (5 ml) under argon was added, dropwise, a 1.54M solution of n-BuLi (0.6 ml, 0.9 mmol, 1.2 equiv.) at −78° C. This mixture was stirred for 30 minutes at 0° C. After cooling at −78° C., HMPT (1 ml), a solution of (2) above (189 mg, 0.75 mmol, 1 equiv.) in dry TMF (5 ml) was added and the mixture was allowed to react for 15 minutes at this temperature. A solution of (3) above (154 mg, 1.35 mmol, 1.8 equiv.) in dry THF (5 ml) was then added dropwise and stirring continued at the same temperature for 2 hours. The reaction was quenched with a saturated solution of ammonium chloride and the mixture obtained dried over $Na_2SO_4$ and concentrated in vacuo. Purification by column chromatography ($Et_2O$/hexane 6/4) on silica gel afforded the title compound as a colourless oil.

5) (3S, 1R and 1S) 3-[(1,1-Dimethylethoxy)carbonylamino]-4-hydroxy-1-cyano-1 (4',4'-diphenyl butyl)-butane A solution of the nitrile of (4) (1 g, 2.2 mmol) and p-toluene sulfonic acid (82 mg, 0.5 mmol) in absolute ethanol (75 ml) was heated under reflux for 4 hours. The solvent was removed in vacuo and the residue taken up in water (10 ml) and $Et_2O$ (100 ml). The organic layer was washed with brine, dried ($Na_2SO_4$) and concentrated in vacuo. The oil obtained was purified by column chromatography on silica gel (hexane/$Et_2O$: 20/80) to obtain the title compound.

6) Methyl (4R and S, 2S)-2-[(1,1-dimethylethoxy)carbonyl]amino-4-cyano-4 (4',4'-diphenylbutyl)-1 butanoate A mixture of the alcohol of (5) (537 mg), DMF (20 ml), and pyridinium dichromate (PDC, 2.87 g, 7.62 mmol) was vigorously stirred for 12 hours at room temperature. The mixture was then diluted with water (250 ml), acidified to pH 2 with 10% aqueous HCl, and extracted with $Et_2O$ (3×100 ml). The combined extracts were washed with brine and concentrated in vacuo. The oily residue was dissolved in MeOH, and then a solution of $CH_2N_2$ in $Et_2O$ was added until the colour of the solution remained yellow. After 4 hours of stirring, excess HOAc was added and the solvent was evaporated in vacuo. The residual oil was purified by column chromatography on silica gel: hexane/AcOEt (60/40) to give the title compound.

7) Methyl (2S, 4S and R)-2-[(1,1-dimethylethoxy)carbonyl]-amino-4-(1H-tetrazol-5-yl)-4-(4",4"-diphenyl butanyl]-1-butanoate A mixture of the ester of (6) (275 mg, 0.61 mmol) and tributyltin azide (405 mg, 1.22 mmol) was heated at 80° C. for 48 hours. The reaction mixture was taken up in ether, washed with aqueous HCl (1M), dried ($Na_2SO_4$) and concentrated in vacuo. The organic residue was purified by column chromatography on silica gel eluting with a mixture of Hex-$Et_2O$:50—50 AcOEt 100% followed by a mixture of AcOEt-AcOH 99.5/0.5) to yield the title compound.

8) (2S, 4S and R) 2-Amino-4-(1H-tetrazol-5-yl)-4-[(4',4'-diphenyl)-butyl]-butanoic acid A solution of LiOH (150 mg, 3.6 mmol) in water (2 ml) was added to a solution of the ester of (7) (100 mg, 0.2 mmol) in 1.2-dimethoxyethane (2 ml). The mixture was stirred at room temperature for 5 hours. The pH was adjusted to 1 with 10% aqueous HCl, and then the mixture was extracted with $Et_2O$ (3×10 ml). The combined extracts were dried ($Na_2SO_4$) and concentrated in vacuo to yield an oil.

A mixture of AcOH (4 ml) and conc. HCl (2 ml) was added, then stirred at room temperature for 2 hours. Concentration in vacuo afforded a residue which crystallised from ether. The crystals were collected and dried to yield the title compound, m.p. 166° C.

EXAMPLE 5

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 6

Capsules each containing 20 mg of medicament are made as follows:

| | |
|---|---|
| Active ingredient | 20 mg |
| Dried starch | 178 mg |
| Magnesium stearate | 2 mg |
| Total | 200 mg |

The active ingredient, starch and magnesium stearate are passed through a sieve and filled into hard gelatin capsules in 200 mg quantities.

We claim:
1. A compound of the formula

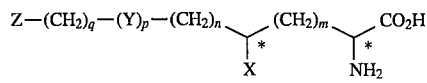

in which m is 1 or 2, n and q are each 0 or 1 to 5, and p is 0 or 1,

X is —$CO_2H$ or tetrazolyl,

Y is —CH=CH—, and

Z is
(i) phenyl, naphthyl or thienyl, said phenyl, naphthyl and thienyl being optionally substituted,
(ii) —$CHR^1R^2$ where $R^1$ and $R^2$ are each phenyl, naphthyl or thienyl, said phenyl, naphthyl and thienyl being optionally substituted, or
(iii)

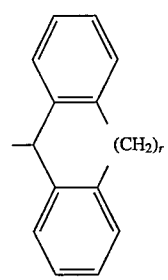

where r is 0 or 1 to 3 and the phenyl rings are optionally substituted;

provided that when Z is phenyl and m is 1, p is 1; or a salt or ester thereof.

2. A compound according to claim 1 in which m is 1.

3. A compound according to claim 2, in which p is 0.

4. A compound according to claim 3 in which X is —CO$_2$H.

5. A compound according to claim 1 which has the enantiomeric structure

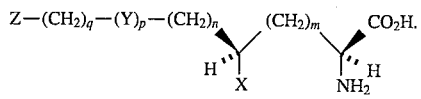

6. A compound according to claim 1 of the formula

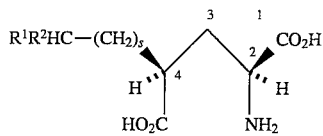

where s is 0 or 1 to 3 and R$^1$ and R$^2$ are both optionally substituted phenyl.

7. A pharmaceutical formulation comprising a compound according to claim 1 or a pharmaceutically acceptable salt or ester thereof, together with a pharmaceutically acceptable diluent or carrier therefor.

* * * * *